United States Patent
Luo et al.

(10) Patent No.: US 11,680,255 B2
(45) Date of Patent: Jun. 20, 2023

(54) GLUCOAMYLASE TLGA15 AND GENE AND APPLICATION THEREOF

(71) Applicant: FEED RESEARCH INSTITUTE, CHINESE ACADEMY OF AGRICULTURAL SCIENCES, Beijing (CN)

(72) Inventors: Huiying Luo, Beijing (CN); Bin Yao, Beijing (CN); Yujie Guo, Beijing (CN); Tao Tu, Beijing (CN); Yuan Wang, Beijing (CN); Huoqing Huang, Beijing (CN); Yingguo Bai, Beijing (CN); Xiaoyun Su, Beijing (CN); Yaru Wang, Beijing (CN); Kun Meng, Beijing (CN)

(*) Notice: Subject to any disclaimer, the term of this patent is extended or adjusted under 35 U.S.C. 154(b) by 93 days.

(21) Appl. No.: 17/283,565

(22) PCT Filed: Sep. 30, 2019

(86) PCT No.: PCT/CN2019/109372
§ 371 (c)(1),
(2) Date: Apr. 8, 2021

(87) PCT Pub. No.: WO2020/073866
PCT Pub. Date: Apr. 16, 2020

(65) Prior Publication Data
US 2021/0340514 A1    Nov. 4, 2021

(30) Foreign Application Priority Data

Oct. 9, 2018    (CN) .......................... 201811171887.5

(51) Int. Cl.
*C12N 9/34*    (2006.01)

(52) U.S. Cl.
CPC .... *C12N 9/2428* (2013.01); *C12Y 302/01003* (2013.01)

(58) Field of Classification Search
CPC .................. C12Y 302/01003; C12N 9/2428
See application file for complete search history.

(56) References Cited

U.S. PATENT DOCUMENTS

2021/0163911 A1* 6/2021 Wang .................. C12N 9/2428

OTHER PUBLICATIONS

Sadowski et al., The sequence-structure relationship and protein function prediction. Current Opinion in Structural Biology, 2009, vol. 19: 357-362. (Year: 2009).*
Seffernick et al., Melamine deaminase and Atrazine chlorohydrolase: 98 percent identical but functionally different. J. Bacteriol., 2001, vol. 183 (8): 2405-2410. (Year: 2001).*
Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: Mar. 18, 2012, pp. 1-10. (Year: 2013).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — Patshegen IP; Moshe Pinchas

(57) ABSTRACT

The present invention relates to the field of genetic engineering, particularly to a glucoamylase TIGa15, gene and application thereof. Said glucoamylase comprises the amino acid sequence of SEQ ID NO:1 or SEQ ID NO:2 and has the excellent enzymic properties, which can be applied to feed, food, and medicine industries, can be industrially produce with the genetic engineering technics.

Figure 1:
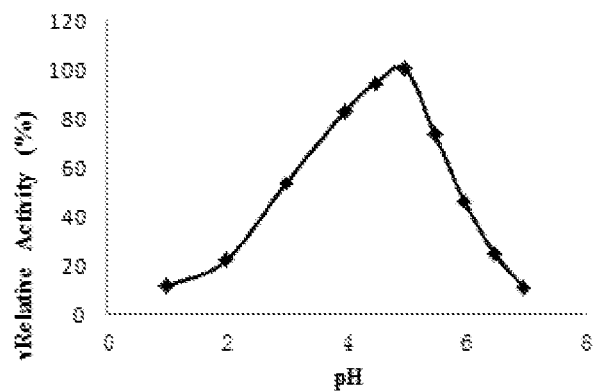

6 Claims, 2 Drawing Sheets
Specification includes a Sequence Listing.

SEQUENCE LISTING

<160> NUMBER OF SEQ ID NOS: 9

<210> SEQ ID NO 1

<211> LENGTH: 613
<212> TYPE: PRT
<213> ORGANISM: Talaromyces bacillisporus

<400> SEQUENCE: 1

Met Gln Tyr Leu Leu Lys Thr Thr Leu Gly Ala Leu Ser Val Ala Gln
1               5                   10                  15

Leu Val Ile Ala Ala Pro His Pro Thr Glu Leu Leu Pro Arg Ala Ser
            20                  25                  30

Gly Ser Leu Asp Ser Trp Leu Ser Thr Glu Val Pro Tyr Ala Leu Asp
        35                  40                  45

Gly Val Leu Asn Asn Ile Gly Pro Asn Gly Ala Lys Ala Gln Gly Ala
    50                  55                  60

Ser Ser Gly Ile Val Val Ala Ser Pro Ser Thr Ser Asn Pro Asp Tyr
65                  70                  75                  80

Phe Tyr Ser Trp Thr Arg Asp Ala Ala Leu Thr Ile Lys Cys Leu Ile
                85                  90                  95

Asp Glu Phe Ile Ser Thr Gly Asp Ala Asn Leu Gln Ser Val Ile Gln
            100                 105                 110

Asn Tyr Ile Ser Ser Gln Ala Phe Leu Gln Thr Val Ser Asn Pro Ser
        115                 120                 125

Gly Gly Leu Ser Thr Gly Gly Leu Gly Glu Pro Lys Phe Glu Val Asn
    130                 135                 140

Glu Ala Ala Phe Thr Gly Ala Trp Gly Arg Pro Gln Arg Asp Gly Pro
145                 150                 155                 160

Ala Leu Arg Ala Thr Ala Met Ile Asn Tyr Ala Asn Trp Leu Ile Ala
                165                 170                 175

Asn Gly Gln Ala Ser Leu Ala Asn Ser Ile Val Trp Pro Ile Val Gln
            180                 185                 190

Asn Asp Leu Ser Tyr Val Ser Gln Tyr Trp Asn Gln Ser Thr Phe Asp
        195                 200                 205

Leu Trp Glu Glu Ile Asp Ser Ser Phe Phe Thr Thr Ala Val Gln
    210                 215                 220

His Arg Ala Leu Val Glu Gly Ser Ala Leu Ala Lys Lys Leu Gly His
225                 230                 235                 240

Thr Cys Ser Asn Cys Asp Ser Gln Ala Pro Leu Val Leu Cys Phe Leu
                245                 250                 255

Gln Ser Tyr Trp Thr Gly Ser Tyr Ile Leu Ser Asn Thr Gly Gly Gly
            260                 265                 270

Arg Ser Gly Lys Asp Ala Asn Ser Leu Leu Gly Ser Ile His Thr Phe
        275                 280                 285

Asp Pro Ala Ala Ala Gly Cys Asp Asp Thr Thr Phe Gln Pro Cys Ser
    290                 295                 300

Ala Arg Ala Leu Ala Asn His Lys Val Val Thr Asp Ser Phe Arg Ser
305                 310                 315                 320

Ile Tyr Ser Ile Asn Ser Gly Ile Pro Gln Gly Gln Ala Val Ala Val
                325                 330                 335

Gly Arg Tyr Pro Glu Asp Val Tyr Gln Gly Gly Asn Ala Trp Tyr Leu
            340                 345                 350

Cys Thr Leu Ala Ala Ala Glu Gln Leu Tyr Asp Ala Leu Tyr Gln Trp
        355                 360                 365

Asn Arg Ile Gly Ser Leu Thr Ile Thr Asp Val Ser Leu Ala Phe Phe
    370                 375                 380

Gln Asp Leu Tyr Pro Ser Ala Ala Thr Gly Thr Tyr Ser Ser Ser Ser

```
            385                 390                 395                 400
        Ser Thr Tyr Gln Ser Ile Val Ala Ala Val Lys Thr Tyr Ala Asp Gly
                        405                 410                 415

Tyr Met Ser Ile Val Gln Lys Tyr Thr Pro Ser Asn Gly Ala Leu Ala
                        420                 425                 430

Glu Gln Phe Ser Arg Asn Asp Gly Ser Pro Leu Ser Ala Val Asp Leu
                        435                 440                 445

Thr Trp Ser Tyr Ala Ser Leu Leu Thr Ala Ala Arg Arg Asn Phe
                450                 455                 460

Ser Val Pro Ala Tyr Ser Trp Gly Glu Ala Ser Ala Asn Thr Val Pro
        465                 470                 475                 480

Ser Ser Cys Ser Ala Ser Ser Ala Ser Gly Pro Tyr Ala Thr Ala Thr
                        485                 490                 495

Asn Thr Asn Trp Pro Ala Pro Thr Cys Thr Ser Pro Ala Asn Val
                        500                 505                 510

Ala Val Arg Phe Asn Glu Met Val Thr Thr Asn Phe Gly Glu Asn Val
                        515                 520                 525

Phe Val Val Gly Ser Ile Ala Ala Leu Gly Ser Trp Ser Pro Ser Ser
                530                 535                 540

Ala Ile Pro Leu Ser Ala Ala Glu Tyr Asn Ser Gln Thr Pro Leu Trp
        545                 550                 555                 560

Tyr Ala Ile Val Thr Leu Pro Ala Gly Thr Ser Phe Gln Tyr Lys Tyr
                        565                 570                 575

Ile Lys Lys Glu Pro Asp Gly Ser Val Val Trp Glu Ser Asp Pro Asn
                        580                 585                 590

Arg Ser Tyr Thr Val Pro Gln Gly Cys Gly Val Thr Thr Ala Thr Val
                        595                 600                 605

Asn Asp Ser Trp Arg
                610

<210> SEQ ID NO 2
<211> LENGTH: 593
<212> TYPE: PRT
<213> ORGANISM: Talaromyces bacillisporus

<400> SEQUENCE: 2

Ala Pro His Pro Thr Glu Leu Leu Pro Arg Ala Ser Gly Ser Leu Asp
        1               5                   10                  15

Ser Trp Leu Ser Thr Glu Val Pro Tyr Ala Leu Asp Gly Val Leu Asn
                        20                  25                  30

Asn Ile Gly Pro Asn Gly Ala Lys Ala Gln Gly Ala Ser Ser Gly Ile
                    35                  40                  45

Val Val Ala Ser Pro Ser Thr Ser Asn Pro Asp Tyr Phe Tyr Ser Trp
                50                  55                  60

Thr Arg Asp Ala Ala Leu Thr Ile Lys Cys Leu Ile Asp Glu Phe Ile
        65                  70                  75                  80

Ser Thr Gly Asp Ala Asn Leu Gln Ser Val Ile Gln Asn Tyr Ile Ser
                        85                  90                  95

Ser Gln Ala Phe Leu Gln Thr Val Ser Asn Pro Ser Gly Gly Leu Ser
                        100                 105                 110

Thr Gly Gly Leu Gly Glu Pro Lys Phe Glu Val Asn Glu Ala Ala Phe
                    115                 120                 125

Thr Gly Ala Trp Gly Arg Pro Gln Arg Asp Gly Pro Ala Leu Arg Ala
                130                 135                 140
```

```
Thr Ala Met Ile Asn Tyr Ala Asn Trp Leu Ile Ala Asn Gly Gln Ala
145                 150                 155                 160

Ser Leu Ala Asn Ser Ile Val Trp Pro Ile Val Gln Asn Asp Leu Ser
                165                 170                 175

Tyr Val Ser Gln Tyr Trp Asn Gln Ser Thr Phe Asp Leu Trp Glu Glu
            180                 185                 190

Ile Asp Ser Ser Ser Phe Phe Thr Ala Val Gln His Arg Ala Leu
        195                 200                 205

Val Glu Gly Ser Ala Leu Ala Lys Lys Leu Gly His Thr Cys Ser Asn
    210                 215                 220

Cys Asp Ser Gln Ala Pro Leu Val Leu Cys Phe Leu Gln Ser Tyr Trp
225                 230                 235                 240

Thr Gly Ser Tyr Ile Leu Ser Asn Thr Gly Gly Arg Ser Gly Lys
                245                 250                 255

Asp Ala Asn Ser Leu Leu Gly Ser Ile His Thr Phe Asp Pro Ala Ala
                260                 265                 270

Ala Gly Cys Asp Asp Thr Thr Phe Gln Pro Cys Ser Ala Arg Ala Leu
        275                 280                 285

Ala Asn His Lys Val Val Thr Asp Ser Phe Arg Ser Ile Tyr Ser Ile
        290                 295                 300

Asn Ser Gly Ile Pro Gln Gly Gln Ala Val Ala Val Gly Arg Tyr Pro
305                 310                 315                 320

Glu Asp Val Tyr Gln Gly Gly Asn Ala Trp Tyr Leu Cys Thr Leu Ala
                325                 330                 335

Ala Ala Glu Gln Leu Tyr Asp Ala Leu Tyr Gln Trp Asn Arg Ile Gly
            340                 345                 350

Ser Leu Thr Ile Thr Asp Val Ser Leu Ala Phe Phe Gln Asp Leu Tyr
        355                 360                 365

Pro Ser Ala Ala Thr Gly Thr Tyr Ser Ser Ser Ser Thr Tyr Gln
370                 375                 380

Ser Ile Val Ala Ala Val Lys Thr Tyr Ala Asp Gly Tyr Met Ser Ile
385                 390                 395                 400

Val Gln Lys Tyr Thr Pro Ser Asn Gly Ala Leu Ala Glu Gln Phe Ser
            405                 410                 415

Arg Asn Asp Gly Ser Pro Leu Ser Ala Val Asp Leu Thr Trp Ser Tyr
            420                 425                 430

Ala Ser Leu Leu Thr Ala Ala Arg Arg Asn Phe Ser Val Pro Ala
        435                 440                 445

Tyr Ser Trp Gly Glu Ala Ser Ala Asn Thr Val Pro Ser Ser Cys Ser
    450                 455                 460

Ala Ser Ser Ala Ser Gly Pro Tyr Ala Thr Ala Thr Asn Thr Asn Trp
465                 470                 475                 480

Pro Ala Pro Thr Cys Thr Ser Pro Ala Asn Val Ala Val Arg Phe
            485                 490                 495

Asn Glu Met Val Thr Thr Asn Phe Gly Glu Asn Val Phe Val Val Gly
            500                 505                 510

Ser Ile Ala Ala Leu Gly Ser Trp Ser Pro Ser Ser Ala Ile Pro Leu
515                 520                 525

Ser Ala Ala Glu Tyr Asn Ser Gln Thr Pro Leu Trp Tyr Ala Ile Val
        530                 535                 540

Thr Leu Pro Ala Gly Thr Ser Phe Gln Tyr Lys Tyr Ile Lys Lys Glu
545                 550                 555                 560

Pro Asp Gly Ser Val Val Trp Glu Ser Asp Pro Asn Arg Ser Tyr Thr
```

565                 570                 575
        Val Pro Gln Gly Cys Gly Val Thr Thr Ala Thr Val Asn Asp Ser Trp
                580                 585                 590
        Arg

<210> SEQ ID NO 3
<211> LENGTH: 1990
<212> TYPE: DNA
<213> ORGANISM: Talaromyces bacillisporus

<400> SEQUENCE: 3

| | | | | | | |
|---|---|---|---|---|---|---|
| ccctcgaggc | atcagggtcc | ctggattcat | ggctttccac | cgaagttcct | tacgctctcg | 60 |
| atggtgtatt | gaacaacatc | ggacccaatg | gtgcaaaggc | ccaggggggcc | agctccggca | 120 |
| tgtggttgc | aagccccagc | acaagtaatc | ctgactgtaa | gtcaacctgc | attcattctg | 180 |
| ctatgaagaa | gcctaactaa | cgcatcctag | acttctactc | ttggactcgg | gacgctgcgc | 240 |
| tcaccatcaa | atgcctgatc | gatgagttca | tctcgactgg | ggatgcgaac | ctgcagtcgg | 300 |
| tgattcagaa | ctatatcagc | tcccaggcct | tcttgcaaac | agtgtccaac | ccctctggcg | 360 |
| gcctgtcaac | tggaggtctc | ggcgagccca | agtttgaggt | caatgaggcg | gcatttactg | 420 |
| gtgcttgggg | ccggccacaa | agagatgggc | cggccttgag | agcgactgcc | atgatcaatt | 480 |
| acgccaactg | gctattgta | agtggttctc | acaggcgagt | acatggctgc | ggtatctgac | 540 |
| gaatgtcatg | ccacaggcaa | atggacaggc | ttcactcgcc | aattcgatcg | tctggccgat | 600 |
| cgtccagaat | gatctctcct | acgtcagcca | gtactggaat | cagagtacct | ttggtacggc | 660 |
| tagtccccca | gagtggcctt | tttctgtact | gacgatgtct | cagacctttg | ggaggaaatc | 720 |
| gacagctcct | ccttcttcac | gacggctgtg | cagcaccgtg | ctcttgttga | gggctctgct | 780 |
| ctggcaaaaa | agcttggcca | tacctgctca | aactgcgact | ctcaagcacc | gcttgtcttg | 840 |
| tgtttcctgc | aatcctactg | gaccggttcc | tatattcttt | ccaacaccgg | agcggacgtt | 900 |
| ccggaaagga | cgccaactcc | ctacttggaa | gtattcatac | ttttgaccag | cagcggcggg | 960 |
| atgcgacgac | accactttcc | agccttgctc | tgcccgagcc | ctagcgaacc | acaaggtcgt | 1020 |
| caccgactcg | ttccgttcaa | tctactcaat | caactcgggc | atcccacagg | gccaagcagt | 1080 |
| cgccgtgggt | cgctaccctg | aagatgtata | tcagggcgga | aacgcatggt | atctctgcac | 1140 |
| cctcgctgct | gcagagcagc | tgtacgacgc | actctatcag | tggaacagga | tcggatctct | 1200 |
| cacgatcacg | gacgtcagct | tggcattctt | ccaggatctc | tacccatcgg | cggcaacagg | 1260 |
| cacttattcc | tcatcctcgt | cgacctacca | atccatcgtt | gccgctgtca | agacgtacgc | 1320 |
| ggacggatac | atgagcattg | ttgtaagtta | ctgcatatcg | ccaagttttt | tccagcgctc | 1380 |
| tcaagagcac | caagtgggaa | aaaaaagtat | aatactcact | aaacccctc | tccaaacagc | 1440 |
| aaaaatacac | cccttccaac | ggcgccctcg | ccgagcagtt | ctcccgcaac | gatggctccc | 1500 |
| ccctctcagc | cgtcgaccta | acctggtcct | acgcctccct | gctcactgcc | gccgcgcgca | 1560 |
| gaaatttctc | cgtccccgcc | tactcctggg | gcgaagccag | cgccaacacc | gtcccatcgt | 1620 |
| cttgctcggc | ctcgtctgcc | tcaggcccct | atgccaccgc | gaccaacacg | aactggcccg | 1680 |
| cacccacatg | cacctcgcca | ccggcaaacg | tggccgtccg | attcaacgag | atggtcacta | 1740 |
| ccaactttgg | agagaacgtc | tttgtcgtgg | gctcgatcgc | cgcgttggga | tcttggagtc | 1800 |
| ctagttccgc | tatcccgctg | agcgcggccg | aatacaactc | acagacgccg | ttgtggtatg | 1860 |
| caatcgtgac | gttgccggcg | ggcacgagct | tccagtataa | gtatatcaag | aaagagccgg | 1920 |

```
atggcagtgt ggtctgggag agtgatccga acaggtccta tacggtgcct caagggtgtg    1980
gcgtgaatta                                                           1990

<210> SEQ ID NO 4
<211> LENGTH: 1842
<212> TYPE: DNA
<213> ORGANISM: Talaromyces bacillisporus

<400> SEQUENCE: 4
atgcagtacc ttcttaaaac taccctcggc gctctgagcg ttgctcagct tgtcatcgcg      60
gcaccacatc ccacggaact tctccctcgg catcagggt ccctggattc atggctttcc     120
accgaagttc cttacgctct cgatggtgta ttgaacaaca tcggacccaa tggtgcaaag     180 gcccagggg ccagctccgg cattgtggtt gcaagcccca gcacaagtaa tcctgactac     240
ttctactctt ggactcggga cgctgcgctc accatcaaat gcctgatcga tgagttcatc     300
tcgactgggg atgcgaacct gcagtcggtg attcagaact atatcagctc ccaggccttc     360
ttgcaaacag tgtccaaccc ctctggcggc ctgtcaactg aggtctcgg cgagcccaag     420 tttgaggtca atgaggcggc atttactggt gcttggggcc ggccacaaag agatgggccg     480
gccttgagag cgactgccat gatcaattac gccaactggc ttattgcaaa tggacaggct     540
tcactcgcca attcgatcgt ctggccgatc gtccagaatg atctctccta cgtcagccag     600
tactggaatc agagtacctt tgacctttgg gaggaaatcg acagctcctc cttcttcacg     660
acggctgtgc agcaccgtgc tcttgttgag ggctctgctc tggcaaaaaa gcttggccat     720
acctgctcaa actgcgactc tcaagcaccg cttgtcttgt gtttcctgca atcctactgg     780
accggttcct atattctttc caacaccgga ggcggacgtt ccggaaagga cgccaactcc     840
ctacttggaa gtattcatac ttttgaccca gcagcggcgg gatgcgacga caccactttc     900
cagccttgct ctgcccgagc cctagcgaac acaaggtcg tcaccgactc gttccgttca     960
atctactcaa tcaactcggg catcccacag ggccaagcag tcgccgtggg tcgctaccct    1020
gaagatgtat atcagggcgg aaacgcatgg tatctctgca ccctcgctgc tgcagagcag    1080
ctgtacgacg cactctatca gtggaacagg atcggatctc tcacgatcac ggacgtcagc    1140
ttggcattct tccaggatct ctacccatcg gcggcaacag gcacttattc ctcatcctcg    1200
tcgacctacc aatccatcgt tgccgctgtc aagacgtacg cggacggata catgagcatt    1260
gttcaaaaat acacccctc caacggcgcc ctcgccgagc agttctcccg caacgatggc    1320
tcccccctct cagccgtcga cctaacctgg tcctacgcct ccctgctcac tgccgccgcg    1380
cgcagaaatt tctccgtccc cgcctactcc tggggcgaag ccagcgccaa caccgtccca    1440
tcgtcttgct cggcctcgtc tgcctcaggc ccctatgcca ccgcgaccaa cacgaactgg    1500 cccgcacccca catgcacctc gccaccggca aacgtggccg tccgattcaa cgagatggtc    1560
actaccaact ttggagagaa cgtctttgtc gtgggctcga tcgccgcgtt gggatcttgg    1620
agtcctagtt ccgctatccc gctgagcgcg gccgaataca actcacagac gccgttgtgg    1680
tatgcaatcg tgacgttgcc ggcgggcacg agcttccagt ataagtatat caagaaagag    1740
ccggatggca gtgtggtctg ggagagtgat ccgaacaggt cctatacggt gcctcaaggg    1800
tgtggcgtga cgactgcgac ggtgaatgat agttggaggt ag                       1842

<210> SEQ ID NO 5
<211> LENGTH: 1782
<212> TYPE: DNA
<213> ORGANISM: Talaromyces bacillisporus
```

<400> SEQUENCE: 5

```
gcaccacatc ccacggaact tctccctcgg gcatcagggt ccctggattc atggctttcc       60
accgaagttc cttacgctct cgatggtgta ttgaacaaca tcggacccaa tggtgcaaag      120
gcccagggg ccagctccgg cattgtggtt gcaagcccca gcacaagtaa tcctgactac      180
ttctactctt ggactcggga cgctgcgctc accatcaaat gcctgatcga tgagttcatc      240
tcgactgggg atgcgaacct gcagtcggtg attcagaact atatcagctc ccaggccttc      300
ttgcaaacag tgtccaaccc ctctggcggc ctgtcaactg gaggtctcgg cgagcccaag      360
tttgaggtca atgaggcggc atttactggt gcttggggcc ggccacaaag agatgggccg      420
gccttgagag cgactgccat gatcaattac gccaactggc ttattgcaaa tggacaggct      480
tcactcgcca attcgatcgt ctggccgatc gtccagaatg atctctccta cgtcagccag      540
tactggaatc agagtaccct tgacctttgg gaggaaatcg acagctcctc cttcttcacg      600
acggctgtgc agcaccgtgc tcttgttgag ggctctgctc tggcaaaaaa gcttggccat      660
acctgctcaa actgcgactc tcaagcaccg cttgtcttgt gtttcctgca atcctactgg      720
accggttcct atattctttc caacaccgga ggcggacgtt ccggaaagga cgccaactcc      780
ctacttggaa gtattcatac ttttgaccca gcagcggcgg gatgcgacga caccactttc      840
cagccttgct ctgcccgagc cctagcgaac cacaaggtcg tcaccgactc gttccgttca      900
atctactcaa tcaactcggg catcccacag gccaagcag tcgccgtggg tcgctaccct      960
gaagatgtat atcagggcgg aaacgcatgg tatctctgca ccctcgctgc tgcagagcag    1020
ctgtacgacg cactctatca gtggaacagg atcggatctc tcacgatcac ggacgtcagc    1080
ttggcattct tccaggatct ctacccatcg gcggcaacag gcacttattc ctcatcctcg    1140
tcgacctacc aatccatcgt tgccgctgtc aagacgtacg cggacggata catgagcatt    1200
gttcaaaaat acacccctc caacggcgcc ctcgccgagc agttctcccg caacgatggc    1260
tccccctct cagccgtcga cctaacctgg tcctacgcct ccctgctcac tgccgccgcg    1320
cgcagaaatt tctccgtccc cgcctactcc tggggcgaag ccagcgccaa caccgtccca    1380
tcgtcttgct cggcctcgtc tgcctcaggc ccctatgcca ccgcgaccaa cacgaactgg    1440
cccgcaccca catgcacctc gccaccggca aacgtggccg tccgattcaa cgagatggtc    1500
actaccaact ttggagagaa cgtctttgtc gtgggctcga tcgccgcgtt gggatcttgg    1560
agtcctagtt ccgctatccc gctgagcgcg gccgaataca actcacagac gccgttgtgg    1620
tatgcaatcg tgacgttgcc ggcgggcacg agcttccagt ataagtatat caagaaagag    1680
ccggatggca gtgtggtctg ggagagtgat ccgaacaggt cctatacggt gcctcaaggg    1740
tgtggcgtga cgactgcgac ggtgaatgat agttggaggt ag                       1782
```

<210> SEQ ID NO 6
<211> LENGTH: 20
<212> TYPE: PRT
<213> ORGANISM: Talaromyces bacillisporus

<400> SEQUENCE: 6

Met Gln Tyr Leu Leu Lys Thr Thr Leu Gly Ala Leu Ser Val Ala Gln
1               5                   10                  15

Leu Val Ile Ala
            20

<210> SEQ ID NO 7

```
<211> LENGTH: 60
<212> TYPE: DNA
<213> ORGANISM: Talaromyces bacillisporus

<400> SEQUENCE: 7
atgcagtacc ttcttaaaac taccctcggc gctctgagcg ttgctcagct tgtcatcgcg      60

<210> SEQ ID NO 8
<211> LENGTH: 34
<212> TYPE: DNA
<213> ORGANISM: Artificial Sequence
<220> FEATURE:
<223> OTHER INFORMATION: synthesized primer

<400> SEQUENCE: 8
ggggaattcg caccacatcc cacggaactt ctcc                                  34

<210> SEQ ID NO 9
<211> LENGTH: 40
<212> TYPE: DNA
<213> ORGANISM: Artificial Sequence
<220> FEATURE:
<223> OTHER INFORMATION: synthesized primer

<400> SEQUENCE: 9
tatgcggccg cctacctcca actatcattc accgtcgcag                            40
```

GLUCOAMYLASE TLGA15 AND GENE AND APPLICATION THEREOF

FIELD OF THE INVENTION

The present invention relates to the field of genetic engineering, particularly to a glucoamylase TlGa15, gene and application thereof.

BACKGROUND OF THE INVENTION

Amylase is a widely used biocatalyst in bread making industry, starch saccharification and liquefaction, textile desizing, papermaking, detergent industry, chemistry, clinical medicine analysis and pharmaceutical industry. Amylase family includes α-amylase, β-amylase and glucoamylase, wherein α-amylase is an endonuclease hydrolyzing α-1,4 glycosidic bond of the starch molecule into dextrin and oligosaccharide, β-amylase is an exonuclease cleaving maltose from non-reducing end in order, and glucoamylase is a kind of exonuclease hydrolyzing α-1,4-glucoside bond known as α-1,4-glucan glucohydrolase (EC. 3.2.1.3) or γ-amylase referred as glucoamylase. Glucoamylase cleaves glucose molecules from the nonreducing sugar end, has lower specificity to the substrate capable of hydrolyzing α-1,4-glycosidic bond, and slightly hydrolyzing α-1,6-glycosidic bond and α-1,3-glycosidic bond, which is widely used to convert amylase hydrolysate into glucose which is converted into industrial products in industries such as food, medicine, and fermentation industries.

It has been reported that glucoamylase is widely distributed in microorganisms such as bacteria, fungi and yeast including Aspergillus, Rhizopus, Pythium, Trichoderma and Penicillium, and has the optimum temperature of 55 to 60° C., and the optimum pH of 3.5 to 5.0. However, the starch usually is liquefied at 95° C. in the industrial practice far higher than the optimum temperature of the existing saccharifying enzymes, resulting in incapability of hydrolyzing amylase at high temperature.

Order of the Invention

In order to solve the problem of low optimal temperature of the glucoamylase in the prior art, the invention provides a glucoamylase and its gene and application.

One order of the present invention is to provide a glucoamylase.

Another order of the present invention is to provide a gene encoding the above glucoamylase.

Another order of the present invention is to provide a DNA construct comprising the gene encoding the above glucoamylase.

Another order of the present invention is to provide a recombinant cell comprising the gene encoding the above glucoamylase.

Another order of the present invention is to provide a method of preparing glucoamylase.

Another order of the present invention is to provide a use of the above glucoamylase.

SUMMARY OF THE INVENTION

In one aspect, the present invention provides a glucoamylase comprising the amino acid sequence of SEQ ID NO:1, with optimum pH of 5.0, good thermostability and an optimum temperature of 65° C.

```
                                              SEQ ID NO: 1
  1  MQYLLKTTLGALSVAQLVIAAPHPTELLPRASGSLDSWLS
 41  TEVPYALDGVLNNIGPNGAKAQGASSGIVVASPSTSNPDY
 81  FYSWTRDAALTIKCLIDEFISTGDANLQSVIQNYISSQAF
121  LQTVSNPSGGLSTGGLGEPKFEVNEAAFTGAWGRPQRDGP
161  ALRATAMINYANWLIANGQASLANSIVWPIVQNDLSYVSQ
201  YWNQSTFDLWEEIDSSSFFTTAVQHRALVEGSALAKKLGH
241  TCSNCDSQAPLVLCFLQSYWTGSYILSNTGGGRSGKDANS
281  LLGSIHTFDPAAAGCDDTTFQPCSARALANHKVVTDSFRS
321  IYSINSGIPQGQAVAVGRYPEDVYQGGNAWYLCTLAAAEQ
361  LYDALYQWNRIGSLTITDVSLAFFQDLYPSAATGTYSSSS
401  STYQSIVAAVKTYADGYMSIVQKYTPSNGALAEQFSRNDG
441  SPLSAVDLTWSYASLLTAAARRNFSVPAYSWGEASANTVP
481  SSCSASSASGPYATATNTNWPAPTCTSPPANVAVRFNEMV
521  TTNFGENVFVVGSIAALGSWSPSSAIPLSAAEYNSQTPLW
561  YAIVTLPAGTSFQYKYIKKEPDGSVVWESDPNRSYTVPQG
601  CGVTTATVNDSWR*
```

According to an embodiment of the present invention, the glucoamylase with a signal peptide of 20 amino acids "MQYLLKTTLGALSVAQLVIA" (SEQ ID NO: 6) in N-terminal comprises 613 amino acids, and the mature glucoamylase comprising the amino acid sequence of SEQ ID NO:2 has a theoretical molecular weight of 63.3 kDa, an optimum pH of 5.0, good thermostability and an optimum temperature of 65° C.

```
                                              SEQ ID NO: 2
  1  APHPTELLPR ASGSLDSWLS TEVPYALDGV LNNIGPNGAK
 41  AQGASSGIVVASPSTSNPDYFYSWTRDAALTIKCLIDEFI
 81  STGDANLQSVIQNYISSQAFLQTVSNPSGGLSTGGLGEPK
121  FEVNEAAFTGAWGRPQRDGPALRATAMINYANWLIANGQA
161  SLANSIVWPIVQNDLSYVSQYWNQSTFDLWEEIDSSSFFT
201  TAVQHRALVEGSALAKKLGHTCSNCDSQAPLVLCFLQSYW
241  TGSYILSNTGGGRSGKDANSLLGSIHTFDPAAAGCDDTTF
281  QPCSARALANHKVVTDSFRSIYSINSGIPQGQAVAVGRYP
321  EDVYQGGNAWYLCTLAAAEQLYDALYQWNRIGSLTITDVS
361  LAFFQDLYPSAATGTYSSSSSTYQSIVAAVKTYADGYMSI
401  VQKYTPSNGALAEQFSRNDGSPLSAVDLTWSYASLLTAAA
441  RRNFSVPAYSWGEASANTVPSSCSASSASGPYATATNTNW
481  PAPTCTSPPANVAVRFNEMVTTNFGENVFVVGSIAALGSW
521  SPSSAIPLSAAEYNSQTPLWYAIVTLPAGTSFQYKYIKKE
561  PDGSVVWESDPNRSYTVPQGCGVTTATVNDSWR*
```

According to an embodiment of the present invention, the glucoamylase has the optimum temperature of 65° C., the optimum pH of 5.0, and good thermostability; and comprises the amino acid sequence of SEQ ID No: 1 or SEQ ID No. 2, or the amino acid sequence having 90% to 99% identity to that of SEQ ID No: 1 or SEQ ID No: 2.

In a preferred embodiment, a glucoamylase is such an active protein that is at least about 90% to 99%, more preferably at least about 90%, 91%, 92%, 93%, 94%, 95%, 96%, 97%, 98%, or 99% homologous to the full amino acid sequence of SEQ ID NO:1 or SEQ ID NO:2, and has the optimum temperature of 65° C., the optimum pH of 5.0, and good thermostability.

In another aspect, present invention provides gene encoding above glucoamylase.

According to an embodiment, a polynucleotide comprises a nucleotide sequence of SEQ ID NO:3 encoding a glucoamylase having the optimum temperature of 65° C., the optimum pH of 5.0, and good thermostability.

```
                                           SEQ ID NO: 3
   1 CCCTCGAGGCATCAGGGTCCCTGGATTCATGGCTTTCCACCGAA
     GTTCCT
  51 TACGCTCTCGATGGTGTATTGAACAACATCGGACCCAATGGTGC
     AAAGGC
 101 CCAGGGGGCCAGCTCCGGCATTGTGGTTGCAAGCCCCAGCACAA
     GTAATC
 151 CTGACTGTAAGTCAACCTGCATTCATTCTGCTATGAAGAAGCCT
     AACTAA
 201 CGCATCCTAGACTTCTACTCTTGGACTCGGGACGCTGCGCTCAC
     CATCAA
 251 ATGCCTGATCGATGAGTTCATCTCGACTGGGGATGCGAACCTGC
     AGTCGG
 301 TGATTCAGAACTATATCAGCTCCCAGGCCTTCTTGCAAACAGTG
     TCCAAC
 351 CCCTCTGGCGGCCTGTCAACTGGAGGTCTCGGCGAGCCCAAGTT
     TGAGGT
 401 CAATGAGGCGGCATTTACTGGTGCTTGGGGCCGGCCACAAAGAG
     ATGGGC
 451 CGGCCTTGAGAGCGACTGCCATGATCAATTACGCCAACTGGCTT
     ATTGTA
 501 AGTGGTTCTCACAGGCGAGTACATGGCTGCGGTATCTGACGAAT
     GTCATG
 551 CCACAGGCAAATGGACAGGCTTCACTCGCCAATTCGATCGTCTG
     GCCGAT
 601 CGTCCAGAATGATCTCTCCTACGTCAGCCAGTACTGGAATCAGA
     GTACCT
 651 TTGGTACGGCTAGTCCCCCAGAGTGGCCTTTTTCTGTACTGACG
     ATGTCT
 701 CAGACCTTTGGGAGGAAATCGACAGCTCCTCCTTCTTCACGACG
     GCTGTG
 751 CAGCACCGTGCTCTTGTTGAGGGCTCTGCTCTGGCAAAAAAGCT
     TGGCCA
 801 TACCTGCTCAAACTGCGACTCTCAAGCACCGCTTGTCTTGTGTT
     TCCTGC
 851 AATCCTACTGGACCGGTTCCTATATTCTTTCCAACACCGGAGCG
     GACGTT
 901 CCGGAAAGGACGCCAACTCCCTACTTGGAAGTATTCATACTTTT
     GACCAG
 951 CAGCGGCGGGATGCGACGACACCACTTTCCAGCCTTGCTCTGCC
     CGAGCC
1001 CTAGCGAACCACAAGGTCGTCACCGACTCGTTCCGTTCAATCTA
     CTCAAT
1051 CAACTCGGGCATCCCACAGGGCCAAGCAGTCGCCGTGGGTCGCT
     ACCCTG
1101 AAGATGTATATCAGGGCGGAAACGCATGGTATCTCTGCACCCTC
     GCTGCT
1151 GCAGAGCAGCTGTACGACGCACTCTATCAGTGGAACAGGATCGG
     ATCTCT
1201 CACGATCACGGACGTCAGCTTGGCATTCTTCCAGGATCTCTACC
     CATCGG
1251 CGGCAACAGGCACTTATTCCTCATCCTCGTCGACCTACCAATCC
     ATCGTT
1301 GCCGCTGTCAAGACGTACGCGGACGGATACATGAGCATTGTTGT
     AAGTTA
1351 CTGCATATCGCCAAGTTTTTTCCAGCGCTCTCAAGAGCACCAAG
     TGGGAA
1401 AAAAAGTATAATACTCACTAAACCCCTTCTCCAAACAGCAAAA
     ATACAC
1451 CCCTTCCAACGGCGCCCTCGCCGAGCAGTTCTCCCGCAACGATG
     GCTCCC
1501 CCCTCTCAGCCGTCGACCTAACCTGGTCCTACGCCTCCCTGCTC
     ACTGCC
1551 GCCGCGCGCAGAAATTTCTCCGTCCCCGCCTACTCCTGGGGCGA
     AGCCAG
1601 CGCCAACACCGTCCCATCGTCTTGCTCGGCCTCGTCTGCCTCAG
     GCCCCT
1651 ATGCCACCGCGACCAACACGAACTGGCCCGCACCCACATGCACC
     TCGCCA
1701 CCGGCAAACGTGGCCGTCCGATTCAACGAGATGGTCACTACCAA
     CTTTGG
```

```
1751 AGAGAACGTCTTTGTCGTGGGCTCGATCGCCGCGTTGGGATCTT
     GGAGTC
1801 CTAGTTCCGCTATCCCGCTGAGCGCGGCCGAATACAACTCACAG
     ACGCCG
1851 TTGTGGTATGCAATCGTGACGTTGCCGGCGGGCACGAGCTTCCA
     GTATAA
1901 GTATATCAAGAAAGAGCCGGATGGCAGTGTGGTCTGGGAGAGTG
     ATCCGA
1951 ACAGGTCCTATACGGTGCCT CAAGGGTGTG GCGTGAATTA
```

According to an embodiment, said polynucleotide encoding a glucoamylase having the optimum temperature of 65° C., the optimum pH of 5.0, and good thermostability contains four introns from +240 to 293 bp, from +582 to 640 bp, from +737 to 786 bp, and from +1428 to 1524 bp and the cDNA sequence has a nucleotide sequence of SEQ ID NO:4 and the length of 1824 bp.

```
SEQ ID NO: 4:
   1 ATGCAGTACCTTCTTAAAACTACCCTCGGCGCTCTGAGCGTTGC
     TCAGCT
  51 TGTCATCGCGGCACCACATCCCACGGAACTTCTCCCTCGGGCAT
     CAGGGT
 101 CCCTGGATTCATGGCTTTCCACCGAAGTTCCTTACGCTCTCGAT
     GGTGTA
 151 TTGAACAACATCGGACCCAATGGTGCAAAGGCCCAGGGGGCCAG
     CTCCGG
 201 CATTGTGGTTGCAAGCCCCAGCACAAGTAATCCTGACTACTTCT
     ACTCTT
 251 GGACTCGGGACGCTGCGCTCACCATCAAATGCCTGATCGATGAG
     TTCATC
 301 TCGACTGGGGATGCGAACCTGCAGTCGGTGATTCAGAACTATAT
     CAGCTC
 351 CCAGGCCTTCTTGCAAACAGTGTCCAACCCCTCTGGCGGCCTGT
     CAACTG
 401 GAGGTCTCGGCGAGCCCAAGTTTGAGGTCAATGAGGCGGCATTT
     ACTGGT
 451 GCTTGGGGCCGGCCACAAAGAGATGGGCCGGCCTTGAGAGCGAC
     TGCCAT
 501 GATCAATTACGCCAACTGGCTTATTGCAAATGGACAGGCTTCAC
     TCGCCA
 551 ATTCGATCGTCTGGCCGATCGTCCAGAATGATCTCTCCTACGTC
     AGCCAG
 601 TACTGGAATCAGAGTACCTTTGACCTTTGGGAGGAAATCGACAG
     CTCCTC
 651 CTTCTTCACGACGGCTGTGCAGCACCGTGCTCTTGTTGAGGGCT
     CTGCTC
 701 TGGCAAAAAAGCTTGGCCATACCTGCTCAAACTGCGACTCTCAA
     GCACCG
 751 CTTGTCTTGTGTTTCCTGCAATCCTACTGGACCGGTTCCTATAT
     TCTTTC
 801 CAACACCGGAGGCGGACGTTCCGGAAAGGACGCCAACTCCCTAC
     TTGGAA
 851 GTATTCATACTTTTGACCCAGCAGCGGCGGGATGCGACGACACC
     ACTTTC
 901 CAGCCTTGCTCTGCCCGAGCCCTAGCGAACCACAAGGTCGTCAC
     CGACTC
 951 GTTCCGTTCAATCTACTCAATCAACTCGGGCATCCCACAGGGCC
     AAGCAG
1001 TCGCCGTGGGTCGCTACCCTGAAGATGTATATCAGGGCGGAAAC
     GCATGG
1051 TATCTCTGCACCCTCGCTGCTGCAGAGCAGCTGTACGACGCACT
     CTATCA
1101 GTGGAACAGGATCGGATCTCTCACGATCACGGACGTCAGCTTGG
     CATTCT
1151 TCCAGGATCTCTACCCATCGGCGGCAACAGGCACTTATTCCTCA
     TCCTCG
1201 TCGACCTACCAATCCATCGTTGCCGCTGTCAAGACGTACGCGGA
     CGGATA
1251 CATGAGCATTGTTCAAAAATACACCCCTTCCAACGGCGCCCTCG
     CCGAGC
1301 AGTTCTCCCGCAACGATGGCTCCCCCCTCTCAGCCGTCGACCTA
     ACCTGG
1351 TCCTACGCCTCCCTGCTCACTGCCGCCGCGCGCAGAAATTTCTC
     CGTCCC
1401 CGCCTACTCCTGGGGCGAAGCCAGCGCCAACACCGTCCCATCGT
     CTTGCT
1451 CGGCCTCGTCTGCCTCAGGCCCCTATGCCACCGCGACCAACACG
     AACTGG
1501 CCCGCACCCACATGCACCTCGCCACCGGCAAACGTGGCCGTCCG
     ATTCAA
1551 CGAGATGGTCACTACCAACTTTGGAGAGAACGTCTTTGTCGTGG
     GCTCGA
```

```
1601 TCGCCGCGTTGGGATCTTGGAGTCCTAGTTCCGCTATCCCGCTG
     AGCGCG
1651 GCCGAATACAACTCACAGACGCCGTTGTGGTATGCAATCGTGAC
     GTTGCC
1701 GGCGGGCACGAGCTTCCAGTATAAGTATATCAAGAAAGAGCCGG
     ATGGCA
1751 GTGTGGTCTGGGAGAGTGATCCGAACAGGTCCTATACGGTGCCT
     CAAGGG
1801 TGTGGCGTGACGACTGCGACGGTGAATGATAGTTGGAGGTAG
```

According to an embodiment, said polynucleotide contains an oligonucleotide sequence encoding the signal peptide,
"ATGCAGTACCTTCTTAAAAC-TACCCTCGGCGCTCTGAGCGTTGCTCAGCTTGTC ATCGCG" (SEQ ID NO: 7), and the polynucleotide encoding the mature glucoamylase having the optimum temperature of 65° C., the optimum pH of 5.0, and good thermostability has a nucleotide sequence of SEQ ID NO:5.

```
SEQ ID NO: 5:
   1 GCACCACATCCCACGGAACTTCTCCCTCGGGCATCAGGGTCCCT
     GGATTC
  51 ATGGCTTTCCACCGAAGTTCCTTACGCTCTCGATGGTGTATTGA
     ACAACA
 101 TCGGACCCAATGGTGCAAAGGCCCAGGGGGCCAGCTCCGGCATT
     GTGGTT
 151 GCAAGCCCCAGCACAAGTAATCCTGACTACTTCTACTCTTGGAC
     TCGGGA
 201 CGCTGCGCTCACCATCAAATGCCTGATCGATGAGTTCATCTCGA
     CTGGGG
 251 ATGCGAACCTGCAGTCGGTGATTCAGAACTATATCAGCTCCCAG
     GCCTTC
 301 TTGCAAACAGTGTCCAACCCCTCTGGCGGCCTGTCAACTGGAGG
     TCTCGG
 351 CGAGCCCAAGTTTGAGGTCAATGAGGCGGCATTTACTGGTGCTT
     GGGGCC
 401 GGCCACAAAGAGATGGGCCGGCCTTGAGAGCGACTGCCATGATC
     AATTAC
 451 GCCAACTGGCTTATTGCAAATGGACAGGCTTCACTCGCCAATTC
     GATCGT
 501 CTGGCCGATCGTCCAGAATGATCTCTCCTACGTCAGCCAGTACT
     GGAATC
 551 AGAGTACCTTTGACCTTTGGGAGGAAATCGACAGCTCCTCCTTC
     TTCACG
 601 ACGGCTGTGCAGCACCGTGCTCTTGTTGAGGGCTCTGCTCTGGC
     AAAAAA
 651 GCTTGGCCATACCTGCTCAAACTGCGACTCTCAAGCACCGCTTG
     TCTTGT
 701 GTTTCCTGCAATCCTACTGGACCGGTTCCTATATTCTTTCCAAC
     ACCGGA
 751 GGCGGACGTTCCGGAAAGGACGCCAACTCCCTACTTGGAAGTAT
     TCATAC
 801 TTTTGACCCAGCAGCGGCGGGATGCGACGACACCACTTTCCAGC
     CTTGCT
 851 CTGCCCGAGCCCTAGCGAACCACAAGGTCGTCACCGACTCGTTC
     CGTTCA
 901 ATCTACTCAATCAACTCGGGCATCCCACAGGGCCAAGCAGTCGC
     CGTGGG
 951 TCGCTACCCTGAAGATGTATATCAGGGCGGAAACGCATGGTATC
     TCTGCA
1001 CCCTCGCTGCTGCAGAGCAGCTGTACGACGCACTCTATCAGTGG
     AACAGG
1051 ATCGGATCTCTCACGATCACGGACGTCAGCTTGGCATTCTTCCA
     GGATCT
1101 CTACCCATCGGCGGCAACAGGCACTTATTCCTCATCCTCGTCGA
     CCTACC
1151 AATCCATCGTTGCCGCTGTCAAGACGTACGCGGACGGATACATG
     AGCATT
1201 GTTCAAAAATACACCCCTTCCAACGGCGCCCTCGCCGAGCAGTT
     CTCCCG
1251 CAACGATGGCTCCCCCCTCTCAGCCGTCGACCTAACCTGGTCCT
     ACGCCT
1301 CCCTGCTCACTGCCGCCGCGCGCAGAAATTTCTCCGTCCCCGCC
     TACTCC
1351 TGGGGCGAAGCCAGCGCCAACACCGTCCCATCGTCTTGCTCGGC
     CTCGTC
1401 TGCCTCAGGCCCCTATGCCACCGCGACCAACACGAACTGGCCCG
     CACCCA
1451 CATGCACCTCGCCACCGGCAAACGTGGCCGTCCGATTCAACGAG
     ATGGTC
1501 ACTACCAACTTTGGAGAGAACGTCTTTGTCGTGGGCTCGATCGC
     CGCGTT
1551 GGGATCTTGGAGTCCTAGTTCCGCTATCCCGCTGAGCGCGGCCG
     AATACA
```

```
-continued
1601 ACTCACAGACGCCGTTGTGGTATGCAATCGTGACGTTGCCGGCG

GGCACG

1651 AGCTTCCAGTATAAGTATATCAAGAAAGAGCCGGATGGCAGTGT

GGTCTG

1701 GGAGAGTGATCCGAACAGGTCCTATACGGTGCCTCAAGGGTGTG

GCGTGA

1751 CGACTGCGACGGTGAATGATAGTTGGAGGTAG
```

According to an embodiment, said polynucleotide encoding the glucoamylase having the optimum temperature of 65° C., the optimum pH of 5.0, and good thermostability has a nucleotide sequence that is at least about 90% to 99%, more preferably at least about 90%, 91%, 92%, 93%, 94%, 95%, 96%, 97%, 98%, or 99% homologous to that of SEQ ID NO:3.

In another aspect, the present invention provides a DNA construct comprising the gene encoding the above glucoamylase by inserting said gene encoding the above glucoamylase between the suitable the restriction enzyme sites of the vector to operably connect with the expression regulating sequence. In a preferred embodiment of the present invention, the glucoamylase gene was inserted between the sites of EcoR I and Not of the vector pPIC9 and located downstream of the promoter AOX1, under the control and regulation of the promoter AOX1 to obtain the recombinant expression vector pPIC9-Tlga15.

In a yet aspect, the present invention provides a recombinant cell comprising the gene encoding the above glucoamylase.

In a yet another aspect, the present invention provides a method of preparing glucoamylase comprising the steps of transforming an isolated host cell with a DNA construct comprising a polynucleotide which comprises a nucleotide sequence encoding said glucoamylase to obtain a recombinant host cell; cultivating the recombinant host cell to produce the glucoamylase; and recovering the glucoamylase.

In a preferred embodiment of the present invention, said isolated host cell is preferred as the isolated *Pichia pastoris* cell, the isolated *Saccharomyces cerevisiae* cell, or the isolated *Hansenula polymorpha* cell, more preferred as the isolated *Pichic pastoris* GS115cell.

The present invention provides a thermostable glucoamylase TlGA15 capable of maintaining more than 50% of its enzyme activity in the range of pH 2.0 to 10.0, and maintaining 79% and 55% of its enzyme activity after being treated at 55° C. for 60 min and at 60° C. for 60 min respectively, and having optimum pH of 5.0 and optimum temperature of 65° C., which belongs to family 15 of glycosylhydrolases.

In another aspect, the present invention provides a use of the above glucoamylase, wherein said glucoamylase with excellent properties can be produced in Industrialization with genetic engineering techniques and applied to feed, food, and medicine industries.

BRIEF DESCRIPTIONS OF THE DRAWINGS

Figure 2:
Figure 3:
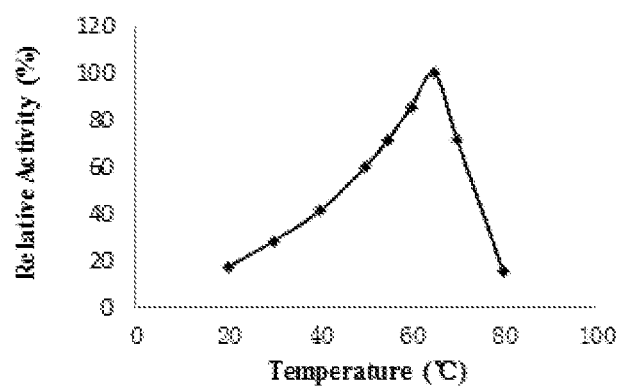
Figure 4:
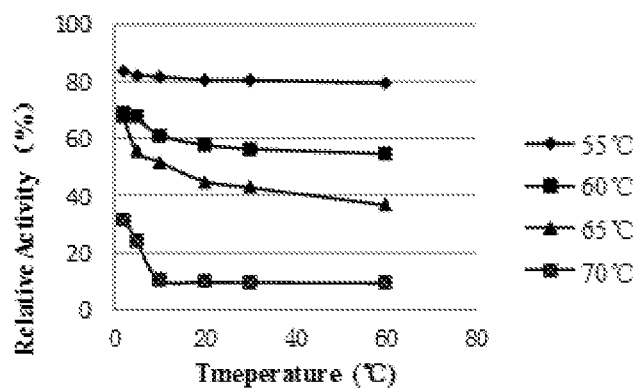

FIG. 1 shows optimum pH values for the recombinant glucoamylase;
FIG. 2 shows pH stabilities for the recombinant glucoamylase;
FIG. 3 shows optimum temperature for the recombinant glucoamylase;
FIG. 4 shows thermostability for the recombinant glucoamylase.

EMBODIMENT

Test Materials and Reagents

1. Strains and Vectors: *Pichia pastoris* Strain GS115; and Vetor pPIC9.
2. Medium:
(1) Enzyme production medium (/L): 30 g/L of bran, 30 g/L of corncob powder, 30 g/L of soybean meal, 5 g/L of barley dextran, 5 g/L of $(NH_4)SO_4$, 1 g/L of $KH_2PO_4$, 0.5 g/L of $MgSO_4.7H_2O$, 0.01 g/L of $FeSO_4.7H_2O$, 0.2 g/L of $CaCl_2$ which were dissolved in 1 L of deionized water, and sterilized for 20 min at 121° C. and 15 pounds.
(2) *E. coli*. LB medium: 1% of peptone, 0.5% of yeast extract, and 1% of NaCl, natural pH.
(3) YPD medium: 2% of glucose, 1% of yeast extract, and 2% of peptone
(4) BMGY medium: 1% of yeast extract; 2% of peptone; 1.34% of YNB, 0.000049% of Biotin; and 0.5% of glycerol (V/V).
(5) BMMY medium: 1% of yeast extract; 2% of peptone; 1.34% of YNB, 0.000049% of Biotin; and 0.5% of methanol (V/V).

Example 1 Cloning Glucoamylase Gene Tlga15

1. Genomic DNA was isolated from *Talaromyces leycettanus* JCM 12802 and performed PCR reaction with the primers as list in table1 using the parameters of 95° C. for 5 min, 30 circles of 94° C. for 30 sec, 50° C. for 30 sec, and 72° C. for 2 min, and 72° C. for 10 min, obtain a polynucleotide fragment in length of about 1800 bp which was recovered and confirmed to compromise the nucleotide sequence of SEQ ID NO: 1 by sequencing.

TABLE 1

Primers

| Primer | SEQUENCE (5'---3') | Length (bp) |
|---|---|---|
| 15F | GGGGAATTCGCACCACATCCCA CGGAACTTCTCC (SEQ ID NO: 8) | 34 |
| 15R | TATGCGGCCGCCTACCTCCAAC TATCATTCACCGTCGCAG (SEQ ID NO: 9) | 40 |

2. Obtaining the cDNA Sequence Encoding the Glucoamylase

The total RNA was isolated from *Talaromyces leycettanus* JCM 12802 and one chain of total cDNA was obtained with Oligo $(dT)_{20}$ and the reverse transcriptas, which was performed PCR with the primers15F and 15R as list in the table 1 followed by being recovered and sequenced to obtain the cDNA sequence of glucoamylase.

And, the obtained cDNA sequence comprised four introns and oligonucleotide sequence encoding the signal peptide comprising 20 amino acids at N-terminal by Blasing, and conformed to be a novel glucoamylase gene from *Talaromyces leycettanus* 12802.

Example 2 Preparing the Recombinant Cell Comprising Glucoamylase Gene

1. Constructing the Expression Vector and Expressing in *Pichiapastoris* GS115

The expression vector pPIC9-Tlga15 comprising the full-length gene encoding glucoamylase was constructed by inserting the gene at the downstream of the signal peptide of the plasmid to form the correct reading frame, followed to transform Ecoli cell Trans1 to screen the positive transformants for sequencing. The transformants with the correct sequence were used to prepare the recombinant plasmid in a large amount. The DNA of the expression vector was lined with restriction enzymes EcoR I and Not I, followed by electronically transforming *Pichia pastoris* strain GS115, and being cultured at 30° C. for 2 to 3 days to screen the transformants on the MD plate for expressing assays.

The recombinant expression vector comprising the gene including the signal peptide was constructed as same as above.

2. Screening the Transformants with High Glucoamylase Activity

The single colony on the MD plate was selected with a sterilized toothpick and numbered on the MD plates which were incubated at 30° C. for 1 to 2 days until the colony grown. The transformants were inoculated in a centrifuge tube containing 3 mL BMGY medium, and cultured according to their number, cultured at 30° C. and 220 RPM for 48 h followed by centrifuging at 3,000×g for 15 min to remove supernatant, and adding 1 mL. BMMY medium containing 0.5% of methanol into the centrifuge tube for induction culturing at 30° C. and 220 RPM for 48 h to collect the supernatant by centrifuging at 3,000×g for 5 min for detecting the activity. Finally, the transformant with high glucoamylase activity were screened out.

Example 3 Producing Recombinant Glucoamylase TlGA15

1. The screened transformants with high enzyme activity were incubated into YPD medium, activated, concentrated and highly expressed on fermentation level. After induction, the supernatant was recovered by spinning at 12,000×g for 10 min to test the activity of the enzyme and performing SDS-PAGE.

2. Purifying the Recombinant Glucoamylase TlGA15

The supernatant of the recombinant glucoamylase TlGA15 expressed in the shaking bottle was collected followed by being concentrated with 10 kDa membrane package while replacing the medium of the fermentation broth with low salt buffer, and further concentrated with 10 kDa ultrafiltration tube. The concentrated solution was further purified with ion exchange chromatography by loading 2.0 mL of glucoamylase TlGA15 concentrate into HiTrap Q Sepharose XL anion column pre-balanced with 20 mM Tris-HCl (pH 6.5), and eluting with NaCL in linear gradient of 0 to 1.0 mol/L, to detect enzyme activity and determine protein concentration of the eluent collected step by step.

Example 4 Measuring the Properties of the Recombinant Glucoamylase

The activity of glucoamylase was measured with DNS method including the steps of performing the enzymatic reaction at 65° C. and pH 5.0 for 30 min, wherein 1 mL of said enzymatic reaction system included 100 μL of appropriate diluted enzyme solution and 900 μL of substrate, terminating the reaction by adding 1.5 ML of DNS, boiling for 5 min, measuring the absorbance at 540 nm and calculating the enzymatic activity after cooling, wherein one unit of enzymatic activity (U) is defined as the amount of enzyme to produce 1 μmol of reducing suga per unit time under given conditions.

1. Optimum pH values and pH stability for the recombinant glucoamylase TlGA15 The glucoamylase purified in example 3 was reacted in the buffers with the different pHs such as glycine hydrochloride series buffer of pH 1.0 to 3.0, citric acid disodium hydrogen phosphate series buffer of pH 3.0 to 9.0, and Glycine NaOH series buffer of pH 9.0 to 12.0 to determine optimum pH.

As shown in FIG. 1, the optimum pH of the glucoamylase is pH 5.0 at 65° C., and the glucoamylase maintains more than 50% of enzyme activity in range of pH3.0 to pH5.5.

Furthermore, pH stability of glucoamylase is researched by determine the enzyme activity after mixing glucoamylase solution with the buffers in different pHs and being treated at 37° C. for 60 min.

As shown in FIG. 2, glucoamylase is capable of maintaining more than 50% of enzyme activity in range of pH2.0 to pH10.0, demonstrating the excellent pH stability of the glucoamylase.

2. Optimum Temperature and Heat Stability of the Recombinant Glucoamylase TlGA15

The glucoamylase was reacted in the different temperatures from 20 to 80° C. at pH 5.0 to determine its optimum temperature. As shown in FIG. 3, the optimum temperature of glucoamylase was 65° C., and it maintained more than 70% of activity at 75° C.

The thermalstability of glucoamylase was determined by detecting the enzyme activity of the of glucoamylase at 60° C. after being treated at the different temperatures for the different time. As shown by FIG. 4, more than 79% of enzyme activity was kept after being treated at 55° C. for 60 min, 55% of enzyme activity was kept after being treated at 60° C. for 60 min, and 24% of enzyme activity was still kept after being treated even at 70° C. for 5 min, demonstrating the excellent thermostability of the glucoamylase.

3. Measuring Enzyme Kinetics and the Specific Activity of the Recombinant Glucoamylase TlGA15

The reaction rate at 65° C. was determined and the values of Km and Vmax were determined by using the double reciprocal plot wherein the glucoamylase TlGA15 was reacted with starch as substrate in different concentrations of 0.4 to 3 mmol/L in 0.1 mol/L of citric acid buffer solution at pH 5.0 at 65° C. for 5 min.

And, Km is 1.86 mg/mL, Vmax is 714 μmol/min/m and the specific activity is 542 U/m after detecting the enzyme activity of glucoamylase TlGA15 using starch as substrate at 65° C.

The invention claimed is:

1. A cDNA construct comprising a nucleotide sequence encoding the glucoamylase with the amino acid sequence of SEQ ID NO:1 or SEQ ID NO:2.

2. The cDNA construct according to claim 1, wherein said nucleotide sequence comprises the nucleotide sequence of SEQ ID NO:3, SEQ ID NO:4 or SEQ ID NO:5.

3. A recombinant strain comprising the cDNA construct of claim 1 or 2.

4. A method for producing the glucoamylase with the amino acid sequence of SEQ ID NO:1 or SEQ ID NO: 2, comprising the steps of transforming an isolated host cell with a cDNA construct comprising the nucleotide sequence encoding said glucoamylase to obtain a recombinant host cell; cultivating the recombinant host cell to produce the glucoamylase; and recovering the glucoamylase.

5. The method according to claim 4, wherein said nucleotide sequence has the nucleotide sequence of SEQ ID NO:3, SEQ ID NO:4 or SEQ ID NO:5.

6. A method of hydrolyzing a α-1,4-glucoside bond, comprising the step of contacting said α-1,4-glucoside bond with a glucoamylase produced by claim 4.

* * * * *